(12) United States Patent
Morrison et al.

(10) Patent No.: US 6,478,750 B1
(45) Date of Patent: Nov. 12, 2002

(54) HAIR COLLECTION DEVICE AND METHODS OF USE THEREOF

(76) Inventors: Janet F. Morrison, 5 Elliott Dr., Simsbury, CT (US) 06070; Peter A. Morrison, 5 Eliot Dr., Simsbury, CT (US) 06070; Carl M. Selavka, 9 Hollywood Dr., Charlton, MA (US) 01507; Thomas M. Eden, 2661 Vesclub Cir., Birmingham, AL (US) 35216; Chip B. Thuss, 2367 Lime Rock Rd., Birmingham, AL (US) 35216; Kenneth C. Hopper, 257 Friends Lake Rd., Chestertown, NY (US) 12817; John S. Sundsmo, 1738 Elevado Rd., Vista, CA (US) 92085

( * ) Notice: Subject to any disclaimer, the term of this patent is extended or adjusted under 35 U.S.C. 154(b) by 147 days.

(21) Appl. No.: 09/715,879

(22) Filed: Nov. 17, 2000

(51) Int. Cl.⁷ ........................... A61B 10/00; B26B 19/00
(52) U.S. Cl. ........................................ 600/564; 30/29.5
(58) Field of Search ............................... 600/562, 564; 30/29.5, 535; 606/222, 133

(56) References Cited

U.S. PATENT DOCUMENTS

| | | | | |
|---|---|---|---|---|
| 2,387,633 A | * | 10/1945 | Alpert et al. | ................. 30/240 |
| 2,686,965 A | * | 8/1954 | Lipman | ...................... 30/29.5 |
| 3,900,252 A | * | 8/1975 | Di Salvo et al. | ............. 353/20 |
| 4,583,562 A | * | 4/1986 | Stewart | ...................... 132/212 |
| 4,811,734 A | * | 3/1989 | McGurk-Burleson et al. | 30/240 |
| 4,867,157 A | * | 9/1989 | McGurk-Burleson et al. | 30/240 |
| 4,931,054 A | * | 6/1990 | Gross | ......................... 30/41.6 |
| 5,895,361 A | * | 4/1999 | Turturro | ..................... 30/124 |
| 6,171,259 B1 | * | 1/2001 | Fisher | ........................ 600/549 |

* cited by examiner

Primary Examiner—William C. Doerrler
(74) Attorney, Agent, or Firm—John S. Sundsmo; BioMedPatent

(57) ABSTRACT

A hair collection device useful in testing for drugs and hazardous materials, comprising an outer barrel with a barrel lumen and a hair collection oriface; an inner hair storage container insertable in and removable from the barrel lumen, and comprising a hair storage lumen and a second hair collection oriface; and a hair snare insertable into the hair storage lumen and extendable through both of the hair collection orifaces.

19 Claims, 4 Drawing Sheets

HAIR COLLECTION DEVICE AND METHODS OF USE THEREOF

FIELD OF THE INVENTION

The invention relates generally to biomedical devices for collecting hair samples useful in analytical testing for exposure to toxins, chemical agents and drugs of abuse.

BACKGROUND OF THE INVENTION

Increased drug abuse in North America has been associated with criminal activities, health problems, newborn addiction, lost worker productivity and staggeringly high medical costs. Currently of greatest concern are opiates, (heroin, morphine, codeine), cocaine, marijuana, MDMA (Ecstasy), phencyclidine, amphetamine and methamphetamine. Costs of workplace problems associated with use of cannabinoids are so great as to be incalculable. It is estimated that cocaine addiction afflicts at least 1.7M individuals in the United States. In 1996 it was suggested that an estimated 4.9M persons in the United States had used methamphetamine at least once, and a study published in 1994 suggested that 16% of high school seniors had used crystal methamphetamine at least once. Surveys suggest that 200–300 million people worldwide, and 20 million in the United States, use marijuana on a regular basis, making it the most widely used drug behind caffeine, alcohol and nicotine.

Drugs of Abuse: Cannabinoids are now known to be fat-soluble psychoactive compounds that can persist in the body for prolonged periods of time. Chronic use of this compound can give rise to cardiovascular effects (e.g., increased pulse rate, tachycardia); pulmonary effects (e.g., bronchitis, increased incidence of cancer); and neurological effects (e.g., impairment in: motor ability, coordination, short term memory, sensory perception, attention, extraction time, psychosis, psychological addiction, mood alteration, confusion and hallucination).

Binding to dopaminergic receptors in the brain and periphery, cocaine interferes with normal pathways of neural transmission. Cocaine addiction can result in acute psychoses, violent behavior and cardiac failure. Personality and behavioral changes associated with cocaine abuse may include euphoria, paranoia, confusion, depression, anxiety, schizoprenia, hallucinations, aggressiveness, short temper, dulled emotions and/or poor concentration. Cardiovascular changes include constricted blood vessels and increases in heart rate, blood pressure and body temperature. Death from cocaine abuse is becoming more common, i.e., resulting from respiratory arrest, heart rhythm disturbances, convulsions and stroke.

It is estimated that more than 14% of intravenous opiate users are HIV-infected.

Urinalysis: Several existing diagnostic systems are marketed for testing cocaine and opiates in urine, e.g., ONTRAK™ and ON- LINE™ (Roche Diagnostic Systems, Inc.), the ADx™ automated fluorescence polarization immunoassay system (Abbott Laboratories, Inc.) and EZ-SCREEN™ (Environmental Diagnostics). Schilling et al., 1999 and Smith et al., 1997 have reported cross-reactivity and performance testing results. Problems with urine testing for drugs of abuse include at least the following issues: namely, (i) rapid elimination rates and short half-life of many compounds can result in a shortened detection window; (ii) false negatives can result from purposeful adulteration and interference (Mikkelsen et al., 1988); (iii) false positive results from cross-reactions with certain medications; and (iv) possible uncertainty can result from cross-reactive substances, e.g., poppy seeds.

Hair Testing: Baumgartner and coworkers (1979) report analysis of human hair for the presence of drugs of abuse and use of radioimmunoassays for detection of opiates hair extracts collected from suspected heroin abusers. In the two decades since that first published report, a variety of additional hair test applications have been disclosed, i.e., for both illicit and therapeutic drugs. Hair provides a unique toxicological specimen. Advantages of hair testing are several. First and foremost, it is more difficult to evade drug detection with hair analysis than with urinalysis because hair testing greatly expands the time window for drug detection compared with more common biological samples, such as urine and serum, i.e., providing information only on recent drug use on the order of hours to day. In contrast, hair grows at approximately 1.5 inches for each 90 days in adults (Saitoh et al.,1969). Following deposition in hair, drugs can persist for extended periods of time, and thus provide information on chronic exposure which can complement the shorter-term information provided by urinalysis. Hair testing also offers opportunities to assess patterns of drug use over time, e.g., relatively constant usage vs. intermittent usage, and/or relative severity of usage, e.g., heavy, intermediate or light. Despite legal challenges regarding constitutionality and admissibility, the results of hair drug testing have been admitted to American courts as scientific evidence in criminal cases, military courts-martial, child custody and adoption cases, and cases involving workplace testing programs.

External Contamination: Probative advantages of hair testing may depend on the ability to distinguish how an analyte has become associated with the sample, in this case, whether it results from external surface contamination of hair, i.e., referred to as "environmental exposure", or from internal, i.e., "physiological", incorporation into hair. "Washability" has been used as one way to assess external contamination. Unfortunately, absolute differences do not appear to exist and variability in different hair sample results is reportedly great (Baumgartner et al., 1996). Variability may result from a variety of intrinsic factors including e.g. differences in the natural porosity of different hairs and/or changes induced by dying (DeLauder et al., 2000). In the laboratory, drugs are commonly extracted from hair samples using organic solvents, acids and bases; in possible combination with, papain and dithiothreitol. Handling of hair samples is tedious with intrinsic potential for contamination of the work surface and laboratory workers. Opportunity also exists for possible inadvertent transfer of hairs between samples.

Sample Integrity: Collection methodology is one key to making an effective determination of drug abuse. To minimize errors from possible mishandling of samples, (as well as attempts at purposeful adulteration), collection devices, test methods and laboratory protocols must all address issues of "sample integrity", i.e., maintaining control of a sample from collection through processing to the final report of a positive or negative test result. While controls exist for insuring and minimizing laboratory cross-contamination, it would be highly desirable to have a secure collection vessel for hair which would also maintain sample integrity by serving as an extraction vessel for drugs and other analytes.

On-Site Testing: While employers wishing to reduce risks in the workplace may currently submit hair samples for laboratory testing, these programs are expensive, i.e., requiring trained personnel and impeccable record keeping to limit legal liability. In the United States, more than 80% of workers are employed by small and medium-sized businesses. To date, it has been difficult to service the needs of these employers with hair testing methodology. It would be highly desirable to have devices capable of assuring sample integrity through the process from collection of a hair sample, while also allowing collection in a relatively non-obtrusive secure manner by ordinary factory, jail, and school personnel.

The Hair Test Sample: The absolute amount of drug which is incorporated into an individual hair is so low as to preclude detection by current quantitative analytical technologies; consequently, the collection of multiple hairs is necessary to effect adequate sensitivity, specificity and precision in a test method. Hair length is also important since the length is directly related to the time over which an individual may have undergone exposure to an agent. Counting and measuring individual hairs is time consuming and imprecise, and offers opportunities for mishandling and loss of sample integrity. It would be highly desirable, particularly for on-site testing, to effect collection of hair samples in a manner that assures routine harvesting of a pre-determined number of hairs.

Objects of the invention provide secure devices for reproducibly collecting homogeneous samples of hair, i.e., containing a pre-determined number of hairs. In other objects the invention provides a device for maintaining sample integrity. In yet other objects, the invention provides a collection device having an extraction vessel wherein analytes of interest may be extracted from hair.

SUMMARY OF THE INVENTION

Hair collection devices are disclosed herein which: (i) collect a pre-determined number of individual hairs for use as a test sample; (ii) minimize sample handling; (iii) maximizing control of sample integrity; (iv) serve as an extraction vessel for dissociating analytes from the hairs in the sample; and, (v) deliver the extract containing the analyte into a detection assay or device without manual intervention, pipetting or special handling. The disclosed hair collection devices safely remove hair from a subject with minimal risk to the operator or subject. The devices allow collection of a hair sample in less than about 10 seconds. Incorrect handling and labeling of samples, is minimized through use of (i) an integrated single unit design; (ii) bar-codable disposable plastic and/or metallic sub-components; (iii) an integral plug-in unit design allowing insertion of the extraction vessel portion of the collection device directly into either laboratory test equipment (e.g., GC/MS) or an on-site immunoassay test device. The devices and methods of the invention find a variety of uses in on-site screening and laboratory test procedures designed to identify exposure to harmful/hazardous materials: e.g., biological agents (e.g., biological toxins and warfare agents), organic chemicals (e.g., toxic benzylic compounds), inorganic metallic compounds (e.g., heavy metal toxins), tobacco products, therapeutic drugs, drugs of abuse and the like.

DETAILED DESCRIPTION OF THE PREFERRED EMBODIMENT

Objects of the invention provide a hair collection device for obtaining measured volumes of hair from a subject, e.g., for use in testing for drugs of abuse, hazardous materials, therapeutic agents and the like. In other objects, the invention provides a hair collection device that minimizes sample handling by personnel during collection and subsequent laboratory (or on-site) analytical procedures. In still other objects, the invention provides a hair collection device capable of delivering a hair sample into a wash and/or extraction vessel without handling. In other objects, the invention provides a hair collection device that incorporates as a sub-component, an extraction vessel useful for extracting analytes from a hair sample. In other objects, the invention provides an integrated single unit design for collecting hair samples and then extracting within the same vessel, analyte compounds. The latter objects reduce risks to laboratory personnel. In other objects, the invention provides collection devices which, due to their integral design, minimizes laboratory risks of cross-contamination and mishandling of test samples taken from different test subjects. In still other objects, the invention provides a hair collection device which comprises a secure hair storage container, i.e., maximizing control of sample integrity. In other objects, the invention provides a disposable hair collection device with an internal extraction device suitable for insertion into an analytical laboratory test system or into an on-site test device.

In other objects, the invention provides methods of using the instant hair collection device to obtain hair samples useful in testing for hazardous materials, e.g., drugs, toxins, chemicals and the like. The subject analytical procedures may be conducted at essentially the same time as sample collection, e.g., in an on-site setting, or they may be conducted at a later time, e.g., in laboratory drug testing facility. In other objects the invention provide methods for using the instant collection device to obtain hair samples from subjects in a safe, secure, rapid and relatively non-invasive manner. In other objects, the instant collection devices and methods offer advantages of simplicity of design and ease of use that enable relatively untrained on-site personnel to, with minimal training, collect hair samples suitable for analytical testing.

The terms employed herein are intended to have meanings as follows: namely, "Proximal" and "Distal" are intended to be directional in the view of an operator of the instant collection device, such that, when grasping the device in a mode suitable for collecting a hair sample from a test subject, i.e., with the base of the unit applied to the scalp at an angle approximating 90-degrees, the distal portion of the instant collection device is located toward the head/scalp of the subject and the proximal portion is located toward the operator; "Hazardous materials" is intended, in the context of the uses envisaged for the instant collection device, to mean a substance capable of producing a dangerous or a harmful effect in a human or a domestic animal. Representative examples of materials so active include biological agents (e.g., biological toxins and warfare agents), organic chemicals (e.g., toxic benzylic compounds), inorganic metallic compounds (e.g., heavy metal toxins), tobacco products, therapeutic drugs, drugs of abuse and the like; "On-site", when used in reference to uses of the instant collection device, is intended to refer to the site at which testing is conducted, e.g., on-site in a factory, school, or jail setting as opposed to conducting a test in a laboratory testing facility; and "Test subject" is intended to mean a human or a domestic animal.

Figure 1A:
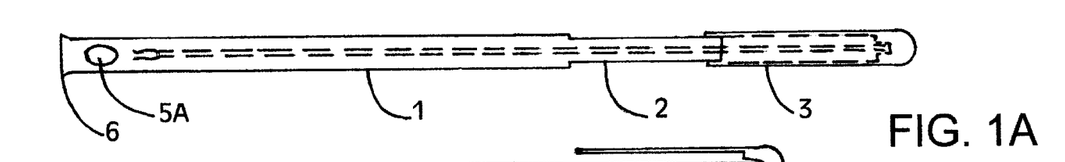
FIG. 1A depicts schematically a hair collection device according to the invention, comprising the following sub-component parts: namely, a hair snare device (FIG. 1B), a barrel portion (FIG. 1C) and a hair collection device/extraction vessel (FIG. 1D), as disclosed further in the Detailed Description section which follows below.
Figures 1B, 1C, 1D, 1E, 1F:
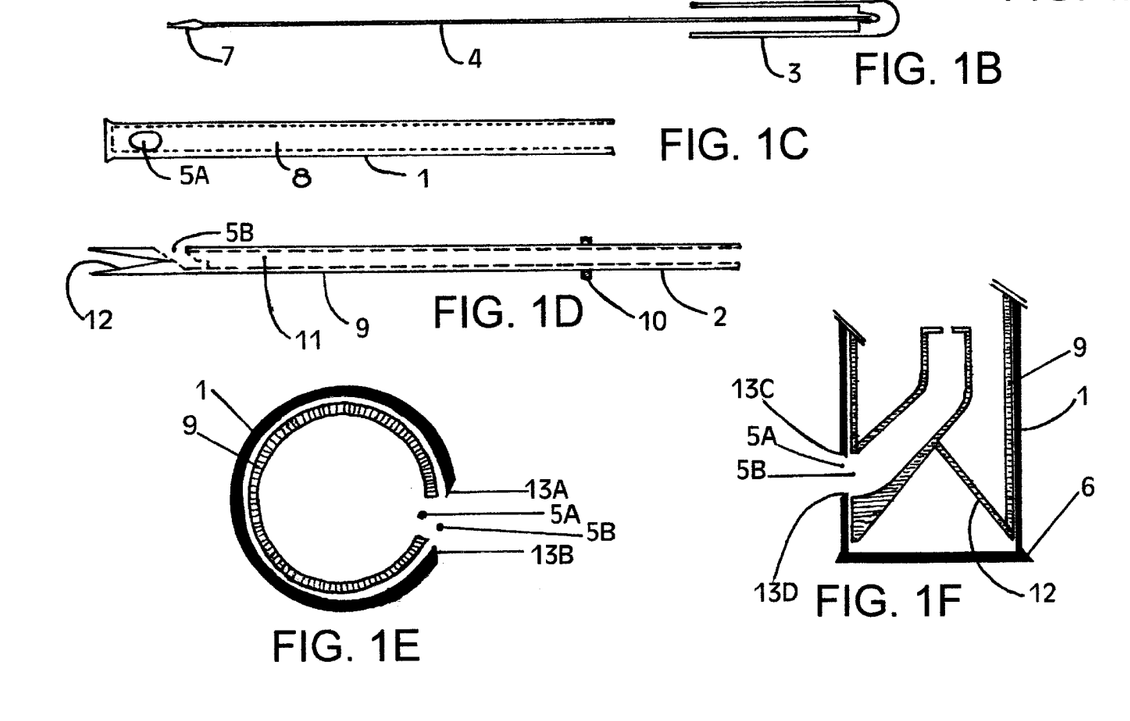
FIG. 1B depicts schematically the hair snare device insertable into the extraction vessel sleeve portion (FIG. 1D) of the hair collection device depicted in FIG. 1A.
FIG. 1C depicts schematically the barrel portion of the hair collection device of FIG. 1A.
FIG. 1D depicts schematically the hair collection/extraction vessel of the hair collection device of FIG. 1A.
FIG. 1E depicts schematically a planar cross-section of the hair collection device of FIG. 1A having both an inner extraction vessel (cross-hatched) and outer barrel (solid) as depicted in FIG. 1D and in FIG. 1C, respectively.
FIG. 1F depicts schematically a longitudinal planar cross-section of the distal portion of the hair collection device of FIG. 1A, i.e., having the inner extraction sleeve portion of FIG. 1D (cross-hatched) and outer barrel portion of FIG. 1C (solid).

Embodiments of the invention provide hair collection devices, according to FIG. 1A, i.e., made up of the sub-component parts schematically depicted in FIG. 1B, FIG. 1C and FIG. 1D. Briefly, an outer barrel 1, depicted in FIG. 1C, serves as a holder for the instant central hair storage/extraction vessel 9 (FIG. 1D) which, in turn, serves as a holder for the instant hair snare device depicted in FIG. 1B.

Referring to FIG. 1A, in one presently preferred embodiment, the instant hair collection device comprises an essentially cylindrical outer barrel 1 which has a central hollow barrel lumen, a distal end plate 6 and a hair capture orifice 5A. Also depicted in this view is: sleeve portion 2 of the hair capture/extraction vessel (FIG. 1D); and, the handle/cap 3 of the hair snare device (FIG. 1B), i.e., as disclosed further below.

Figures 2A, 2B, 2C, 2D:
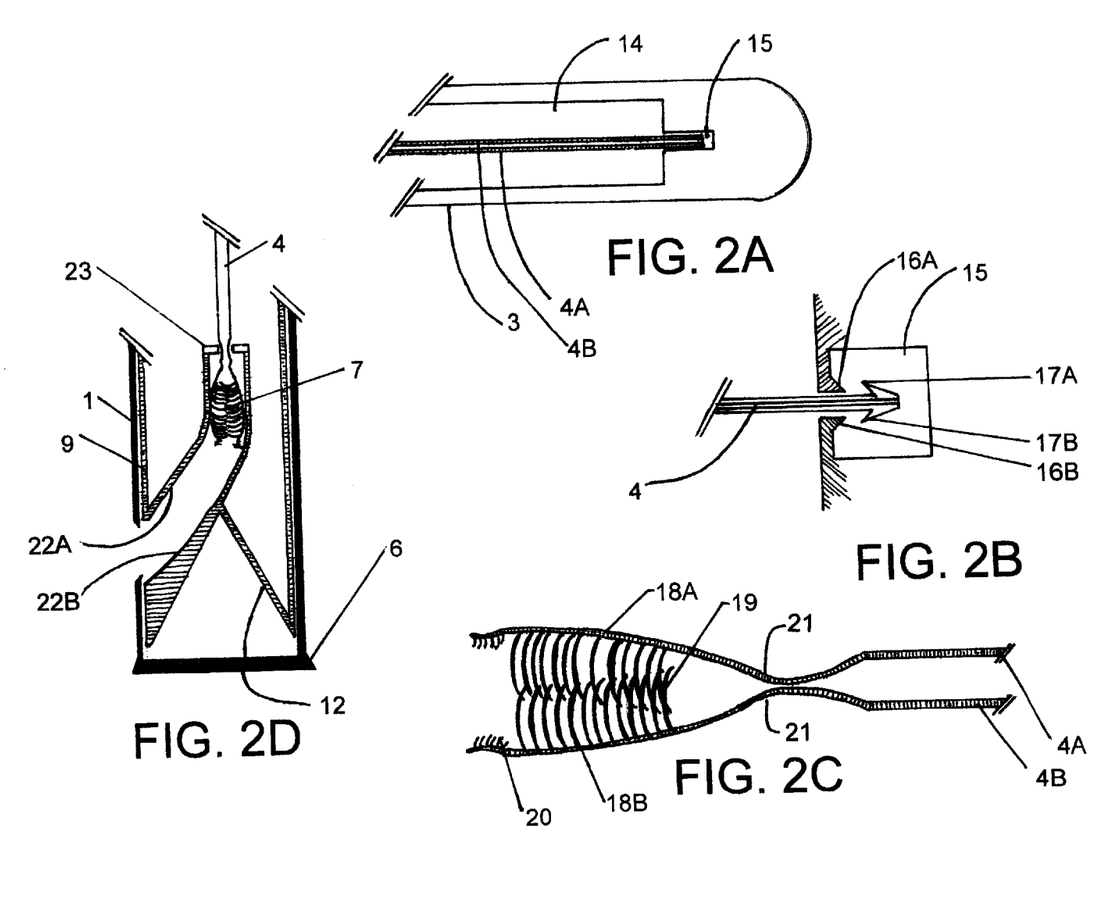
FIG. 2A depicts schematically a longitudinal planar cross-section of the proximal handle/cap portion and shaft (cross-hatch) of the hair snare of FIG. 1B.
FIG. 2B depicts schematically a magnified cross-sectional planar view of a socket region in the handle/cap of FIG. 2A comprising interlocking-means for retaining the hair snare shaft.
FIG. 2C depicts schematically a longitudinal planar cross-section of the hair capture portion located at the distal end of the hair snare of FIG. 1B.
FIG. 2D depicts schematically a magnified longitudinal planar cross-section of the hair collection device of FIG. 1A and FIG. 1F with the inner extraction vessel sleeve of FIG. 1D (cross-hatch) inserted in the barrel portion of FIG. 1C (solid) and with the distal portion of the hair snare of FIG. 1B and FIG. 2C inserted in the storage lumen of the extraction vessel.

Referring to FIG. 1B, the instant hair snare sub-component device comprises a proximally located handle/cap portion 3 (further disclosed in regard to FIG. 2A), a medial shaft portion 4 and a distal hair capture portion 7, (further disclosed in regard to FIG. 2B). The instant hair snare sub-component is slideably insertable into, and removable from, the proximal lumen of sleeve 2 of the hair storage/extraction vessel 9 sub-component (FIG. 1D). The handle/cap portion 3 of the hair snare device is also insertable onto, and slideably engaging on, the sleeve portion 2 of the hollow hair storage/extraction vessel 9, (further disclosed in regard to FIG. 1D, below).

Referring to FIG. 1C, the instant outer barrel 1 of the hair collection device of FIG. 1A comprises a hollow barrel lumen 8 with hair capture orifice 5A and distal base portion 6. The hair storage/extraction vessel 9 (FIG. 1D; below) is insertable within, and removable from, barrel lumen 8. The distal base portion 6 of the barrel is suitable for application to the scalp of a test subject, preferably, without irritation. While the distal base portion 6 of barrel 1 is depicted as a substantially flat plate, a variety of shapes are accommodated, e.g., rounded, suction cup shaped and like, provided that the shape not be irritating to a test subject.

Referring to FIG. 1D, hair storage/extraction vessel 9 is slideably insertable and rotatable within lumen 8 of barrel 1 (FIG. 1C). Storage/extraction vessel 9 in turn, comprises a hollow storage lumen 11 (the margins of which are depicted by dashed lines in FIG. 1D), suitable for receiving and slideably retaining shaft 4 and snare 7 of the hair snare sub-component depicted in FIG. 1B. The wall of storage vessel 9 comprises distal hair capture orifice 5B and proximal sleeve portion 2 for receiving and slideably retaining handle/cap 3 (FIG. 1B). (A distal portion side wall 12 is further disclosed in regard to FIGS. 1F and 2D, below). The hair snare device of FIG. 1B is insertable within the hollow storage lumen 11 of hair storage/extraction vessel 9 and is freely movable in a proximal and distal direction from the proximal boundary of sleeve 2 up to, and stopping at the margin of boss 10. The hair snare device is also freely movable (in a proximal/distal direction) and removable (in a proximal direction) from the proximal boundary of the sleeve portion 2 of storage vessel 9. Boss 10, on its distal surface, is effective to limit travel in a distal direction of the storage/extraction vessel 9 within the lumen 8 of barrel 1.

In a presently preferred embodiment, boss 10 is preferably circular, i.e., surrounding the outer margin of a cylindrical storage/extraction vessel 9. In alternative embodiments, boss 10 may comprise one or more motion restrictors protruding from the surface of extraction vessel 9, e.g., a snap ring received into a recess in the exterior surface of barrel 1, but provided that the subject motion restrictors limit the distal travel of both: (i) the storage/extraction vessel 9 sub-component within the lumen 8 of the barrel 1 sub-component; and, (ii) the hair snare handle/cap 3, i.e., on sleeve 2 of the storage/extraction vessel 9.

FIG. 1E schematically depicts a planar cross-section taken through the hair collection device of FIG. 1A at the location of barrel 1 orifice 5A and storage/extraction vessel 9 orifice 5B. In the latter cross-section, the hair snare device (FIG. 1B) is located proximal to the plane of the cross-section, thus, not visible in this depiction. Inner hair storage/extraction vessel 9 is freely slideable (in a distal-to-proximal direction) and fully rotatable within the lumen 8 of outer barrel 1. The margins of barrel 1 at hair capture orifice 5A comprise lateral cutting surfaces 13A/13B, in this case, located integral with and surrounding the entire peripheral margin of orifice 5A. In operation, rotation of outer barrel 1 about inner storage/extraction vessel 9, or vice versa, is effective in bringing cutting surface 13A/13B into a cutting apposition with hairs that are protruding through both of orifice 5A and orifice 5B.

FIG. 1F is a schematic enlarged depiction of a longitudinal planar cross-section taken through the distal portion of the hair collection device of FIG. 1A, i.e., at the plane of hair collection orifices 5A and 5B, and with inner storage/extraction vessel 9 (FIG. 1D) inserted into barrel 1 lumen 8 (FIG. 1C), but with the hair snare device of FIG. 1B removed to simplify the present disclosure. The margins of outer barrel 1 orifice 5A, as disclosed supra, comprise cutting surfaces, i.e., labeled 13C/13D to identify the proximal and distal surfaces. Orifice surfaces 13C, 13D are capable of cutting hairs protruding through both of orifices 5A and 5B when inner storage/extraction vessel 9 is moved in a proximal direction, i.e., away from barrel base 6. (Details of the distal portion 12 of storage/extraction vessel 9 are disclosed further in regard to FIG. 2D, below.)

Referring to FIG. 2A wherein the handle cap portion 3 of the hair snare device of FIG. 1B is schematically depicted in a longitudinal cross-section view. Handle/cap 3 comprises a hollow sleeve recess 14 capable of engaging both slideably and rotatably on the sleeve portion 2 of storage/extraction vessel 9 (FIG. 1D). Also shown in this cross-section is a partial view of the proximal portion of hair snare shaft 4 which is comprised, in this presently preferred embodiment, of two parallel shaft members 4A/4B. The two shaft members 4A/4B are embedded in, and retained within, cap recess 15. The means for retaining shaft members 4A/4B in this particular embodiment are snap clips 16A/16B depicted in the enlarged view of FIG. 2B. In the latter embodiment of FIG. 2B, snap clips 16A/16B are integral with the walls of cap recess 15 and engage prongs 17A/17B integral with the proximal end of each of shaft members 4A/4B. In other alternative embodiments, it is envisaged that retention of hair snare shaft 4A/4B within cap recess 15 may be accomplished using a variety of cements, glues and adhesive compounds, as well as, a variety of different fasteners.

FIG. 2C, schematically depicts an enlarged view of a planar cross-section of the distal capture portion 7 of the hair snare sub-component of FIG. 1B. The depiction reveals shaft 4A/4B (FIG. 2A) integral with the hair capture portion 7 of the snare. Hair capture portion 7 comprises two mounting members 18A/18B, i.e., integral with shaft 4A/4B. Mounting members 18A/18B are flexible about neck region 21 and to form a flexible angle, the one to the other, ranging from about 5° to about 50°. Each of the subject mounting members 18A and 18B comprise means for retaining a plurality of proximal hair snare fibers 19 and distal hair snare fibers 20. Preferably, mounting members 18A/18B are flexibly compressible and variable in angle about an axis located at a neck region 21 on shaft members 4A/4B, i.e., to achieve an angle of about 5° to about 50° relative to one another, i.e., referred to herein as the "hair capture angle". Neck region 21 preferably has a cross-sectional diameter which is less that the diameter of the proximal region of shaft 4A/4B. Preferably, each of the two mounts 18A/18B have a convex shape originating at neck 21. Most preferably, mounting members 18A/18B extend springably from neck 21 in such manner that each may be compressed, i.e., the one toward the other, and when compressed, may be retained in such compressed mode, i.e., as disclosed further in regard to FIG. 2D, below. In a presently preferred embodiment, hair snare fibers 19 and 20, are mounted substantially perpendicular to the surface of opposing mounting members 18A and 18B, and fibers 19 and 20 are either integral with members 18A and 18B, or alternatively, both of the latter fibers are rigidly retained by members 18A and 18B.

FIG. 2D schematically depicts a longitudinal cross-section through the distal portion of the hair collection device of FIG. 1A showing base 6, the outer barrel 1 of FIG. 1C, the inner hair storage/extraction vessel 9 of FIG. 1D and the distal portion of hair snare device of FIG. 1B, in this case, with hair snare shaft 4 engaged slideably within extraction vessel 9 lumen 11. In the presently preferred embodiment depicted in FIG. 2D, storage lumen 11 comprises a formed cylindrical guide chamber made up, in cross-section, of walls 22A/22B and top cap 23. Chamber top cap 23 has a passage to permit slideable entry, retention and removal of hair snare shaft 4. Preferably, hair snare shaft members 4A and 4B are flexible and compressible, i.e., the one toward the other, such that the pair of members are retained flexibly within the chamber cap passage at neck 21 (FIG. 2C). Preferably, hair snare 7 is retained within the guide chamber formed by the compressive force exerted by chamber walls 22A/22B on mounting members 18A and 18B (FIG. 2C).

In use, an operator grasping the handle/cap 3 portion of the hair snare 4 may force it in a distal direction (i.e., toward the scalp of a test subject); the force being transmitted along shaft 4 into snare 7; snare 7 is thereby driven along guide chamber walls 22A/22B to emerge from orifices 5A/5B. Preferably, snare 7 is both: (i) springably self-opening, i.e., as it emerges from orifices 5A/5B; and, (ii) springably self-closing, i.e., so that when an operator applies a force in a proximal direction, i.e., away from the scalp, snare 7 is springably re-compressed by guide chamber walls 22A/22B.

In presently preferred embodiments, barrel 1 of the hair collection device of FIG. 1A and FIG. 1C is substantially cylindrical in shape with a hollow interior. However, presently envisaged alternative embodiments include devices in which outer barrel 1 and inner collection extraction vessel 9 are both substantially square, or both 1 and 9 are substantially rectangular. Also envisaged are devices in which both of the latter members 1 and 9 assume substantially an elliptical shape, as well as those in which both members 1 and 9 assume a shape composed of one or more arcs, and/or, one or more straight lines; but, with the proviso that the shape of barrel 1 allows extraction vessel 9 to be slideably engaged within, and removed from, its hollow interior. Preferably, the subject shape fulfills the requirements that the subject hair storage/extraction vessel 9 is both insertable into and rotatable within barrel 1 lumen 8. Most preferably, the subject shape of barrel 1 also fulfills the additional requirement that it is easily grasped in one hand of a human operator so that the other hand of the operator may engage, and rotate, hair storage/extraction vessel 9.

In other embodiments, the invention provides methods of using the instant device (of FIGS. 1A–2D) to collect hair samples through the process of: (i) engaging a distal base portion 6 of a hair capture device with the scalp of a test subject; (ii) drawing a hair sample through orifices in both an outer barrel and an inner chamber, e.g., orifices 5A and 5B, wherein the margins of the outer barrel orifice also comprise cutting surfaces 13A–13D; and (iii) wherein cutting the hair sample by rotating an outer barrel 1 about an inner chamber 9 and/or sliding the inner chamber 9 in a proximal direction, both of which actions are effective to cut the hair trapped in orifices 5A/5B and effect collection and storage of the hair in storage/extraction vessel 9 lumen 11.

Figure 3:
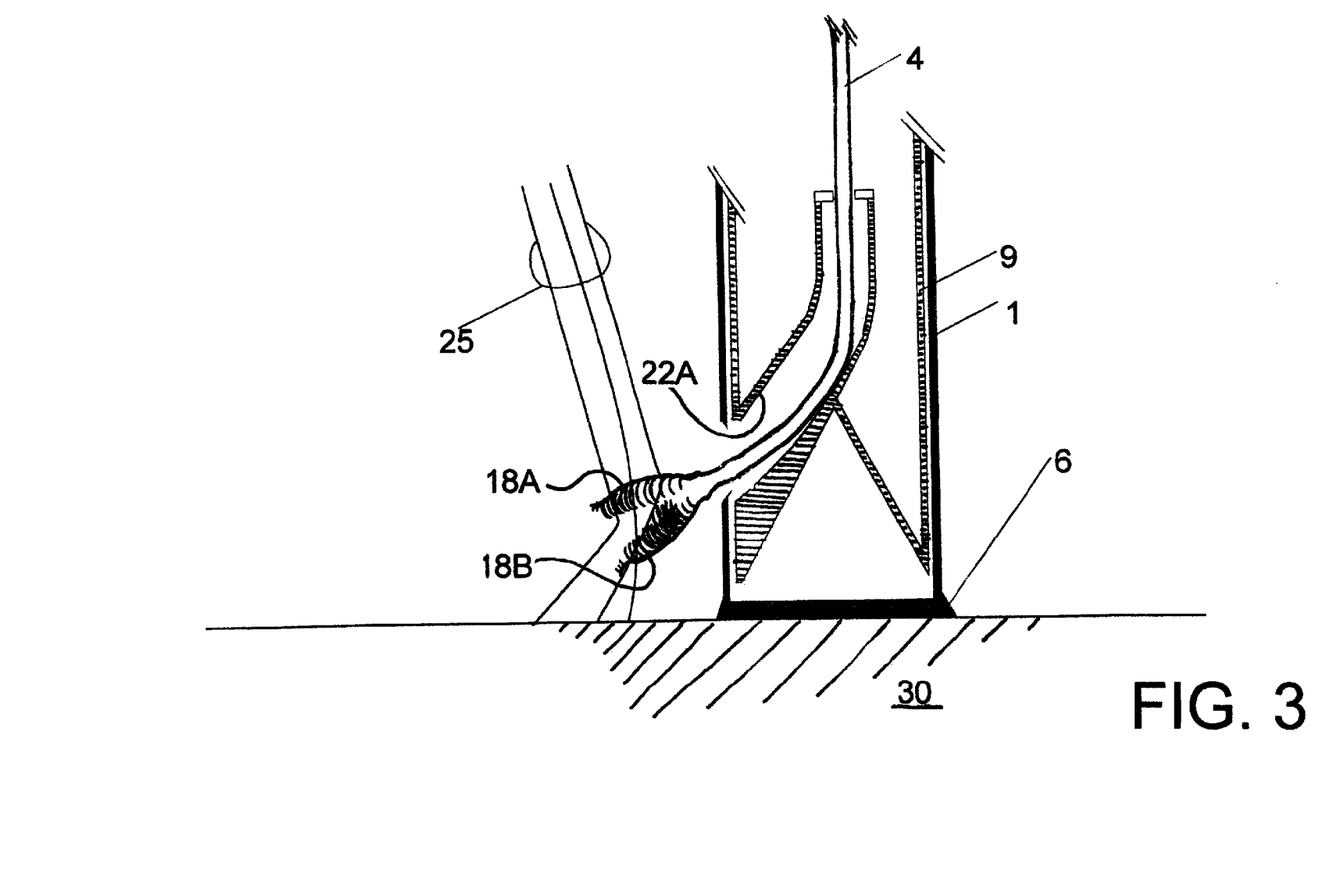
FIG. 3 depicts schematically a longitudinal planar cross-section of the hair collection device of FIG. 1A, FIG. 1F and FIG. 2D, as applied to the scalp of a test subject and with the distal portion of the hair snare of FIG. 1B and FIG. 2C involved in the process of hair collection.

To expand upon the mechanics of operation, in a presently preferred embodiment, force applied by an operator to handle/cap 3 of the hair snare device of FIG. 1B, drives the handle/cap 3 in a distal direction along sleeve 2, thereby exerting a distal driving force on hair snare shaft 4 which, in turn, forces hair capture portion 7 slideably along guide channel 22A/22B to exit the hair collection device through orifices 5A/5B, i.e., as schematically depicted in FIG. 3. Snare hair capture portion 7 is preferably flexibly self-opening (as disclosed supra) allowing snare fibers 19 and 20 to become entangled with hair shafts 25 attached to the scalp 30 of a test subject, i.e., a process referred to herein as "entrapping" and "entrapment of" hair shafts 25. When the operator has fully engaged the handle/cap 3 in a distal direction to the limiting stop provided at storage/extraction vessel 9 boss 10, the next step is to begin withdrawing the hair snare (in a proximal direction) from the storage/extraction vessel 9 lumen 11, and, in the process, compressing the flexibly extended snare 7 back to its original shape as members 18A and 18B (FIG. 2C) engage and then enter guide chamber 22A/22B. Compressible capture of hairs 2 is affected as members 18A and 18B are compressed back to their original shape by the walls 22A/22B of the guide chamber, i.e., a process referred to herein as "compressive hair capture". The hairs 25, so captured, may then be drawn in completely through orifices 5A/5B into guide chamber 22A/22B (FIG. 2D), through chamber top 23, up and into, the expanded storage lumen 11 of storage/extraction vessel 9. At this point, the hair snare device may be completely removed from storage/extraction vessel 9 lumen 11, leaving the captured hair within the storage/extraction vessel. During this entire process care is taken to maintain contact between the hair collection device base 6 and the scalp 30 of the test subject. Next, the operator simultaneously grasps both the sleeve 2 portion of storage/extraction vessel 9 and barrel 1, and then applies rotational and/or proximal force (i.e., away from scalp 30), thereby bringing the cutting surfaces 13A/B/C/D of orifice 5A (FIG. 1E), or orifice 5B (FIG. 4H), into cutting apposition with hair shafts 25. The proximal and/or rotational force applied by the operator is effective to remove the hair collection device from the scalp of the test subject, cut the hair sample loose from the scalp while securely retaining the sample within the storage/extraction vessel 9 lumen 11.

Figures 4A, 4B, 4C, 4D, 4E, 4F:
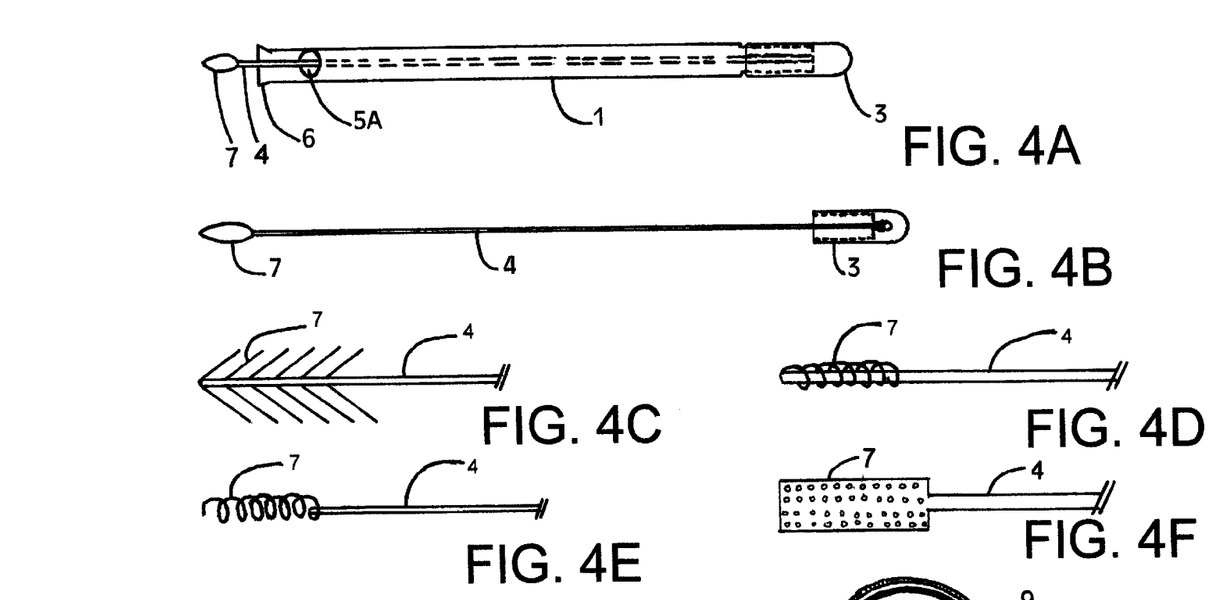
FIG. 4A depicts schematically an alternative embodiment in which the hair snare portion constitutes a loop capture enclosure, as disclosed further below in the Detailed Description of the Invention.
FIG. 4B depicts schematically a magnified view of an alternative hair snare loop capture enclosure of FIG. 4A, as disclosed further below.
FIG. 4C depicts schematically a magnified view of an alternative hair snare brush capture enclosure, as disclosed further below.
FIG. 4D depicts schematically a magnified view of an alternative hair snare coil loop capture enclosure, as disclosed further below.
FIG. 4E depicts schematically a magnified view of an alternative hair snare distal coil loop capture enclosure, as disclosed further below.
FIG. 4F depicts schematically a magnified view of an alternative hair snare adhesive hair capture pad, as disclosed further below.
Figure 4G:
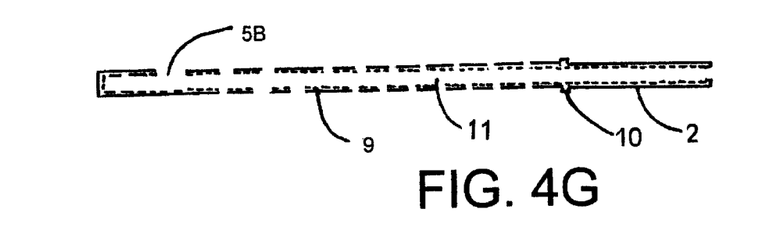
FIG. 4G depicts schematically an alternative perforated extraction vessel, as disclosed further below.

In other embodiments, the invention provides a secure storage/extraction vessel 9 suitable for both collection of a hair sample and subsequent extraction of hazardous materials. Extraction is commonly accomplished by methods known in the art involving addition of organic solvents, acids and bases, or supercritical fluids such as carbon dioxide, e.g., introduced through orifice 5B and/or introduced directly into storage lumen 11 at the proximal entrance in sleeve 2. In an automated laboratory analytical test procedure, storage/extraction vessel 9 sleeve 2 may be used as insertable means for "plugging" the collected hair sample into an automated extraction device, e.g., a fluid-flow extraction device involving sequential stepwise, or continuous, flow of a fluid, (e.g., a supercritical fluid, organic solvent, acid or base), from one end to the other end of extraction vessel 9 toward the other. Alternatively, it may prove desirable to introduce the subject fluid into storage lumen 11 of storage/extraction vessel 9 through perforations, holes, slots and the like, cut (or formed) into the side wall of extraction vessel 2 lumen 11. FIG. 4G schematically depicts such an alternative extraction vessel 9 having perforations in the lumen 11 side walls to allow fluid exchange from outside the vessel into storage lumen 11.

Analysis of the hair wash fluid or hair extract fluid, i.e., from treatments of hair samples contained within extraction vessel 9, may be conducted in a sequential or continuous manner. The subject sequential and/or continuous fluid flow processes may be effective to distinguish environmental contamination of a hair sample, from metabolic incorporation of a drug into hair. Analytical assays that may prove useful for detecting drug analytes in the subject extracts and wash solutions of hair include, e.g. gas chromatography and mass spectrometry (tandem GC/MS), immunoassays and the like.

In other embodiments the invention provides "hair entrapment means" and "compressive hair capture means". A variety of "entrapment means" and "compressive capture means" are currently envisaged. Entrapment means include e.g. (i) the Venus fly trap snare means of FIG. 2C, (ii) the loop means depicted schematically in FIG. 4B, (iii) the brush/comb means depicted schematically in FIG. 4C, (iv) the coil means depicted schematically in FIG. 4D, (v) the spring means depicted schematically in FIG. 4E, (vi) the elastomeric pad means depicted schematically in FIG. 4F, and the like. It is envisaged that the volume of snare 7 will be adjusted to flexibly achieve different hair capture capacities and different hair capture angles. Presently preferred embodiments for analytical testing of drugs of abuse utilize a snare capture volume (FIG. 2C), a loop capture volume (FIG. 4B), a brush/comb capture volume (FIG. 4C), a coil capture volume (FIG. 4D), a spring capture volume (FIG. 4E) and a pad capture volume (FIG. 4F). The instant alternative entrapment means are each individually capable of capturing about 5 to about 50 human hairs; preferably, about 10 to about 50 and most preferably, about 10 to about 20 hairs. Further instruction is provided as follows: namely, In regard to the Venus fly trap hair snare means of FIG. 2C, the spacing, alignment, overall length and curvature of the instant hair snare fibers 19 is such that snare 7 provide "entrapment means" (as defined supra). Structurally, entrapment means comprises:

(i) A spacing, alignment and length of the plurality of snare fibers 19 and 20 that is capable of capturing hair shafts 25 between adjacent fibers 19, such as may be accomplished when opposing mounting members 18A and 18B lie at an angle of greater than about 15° to about 50° relative to on another as schematically depicted in FIG. 3; preferably, the subject angle to affect capture is about 20° to about 50°; most preferably, the subject angle is about 30° to about 45°;

(ii) Hair 25 (FIG. 3), so entrapped, is retained by the subject plurality of snare fibers 19, i.e., within snare 7, when the angle of mounting member 18A to member 18B is less than about 15°; and, at the same time, (iii) Individual hairs, so entrapped, in step (ii), may be pulled in a combing-like-fashion between the adjacent plurality of hair snare fibers 19. The presently preferred shape for the plurality of hair snare fibers 19 is convex, i.e., as depicted in FIG. 2C and FIG. 3, so that as snare 7 moves laterally away from barrel 1 orifice 5A into the midst of the hairs 25 on the scalp 30 (or hide) of a test subject, the subject's hairs push snare 7 into an open position, e.g., at a hair capture angle of greater than about 15°. In this manner the subject's hairs gain entry into snare 7 and the individual hairs become positioning between the respective plurality of snare fibers 19. Preferably, when snare 7 moves laterally back toward barrel 1 orifice 5A the convex shape of fibers 19 helps to retain hairs 25 within snare 7, i.e., in a comb-like manner without pulling irritation to the test subject.

Also in regard to the Venus fly trap hair snare means of FIG. 2C/FIG. 3, the spacing, alignment, overall length and curvature of the instant hair snare fibers 19 is such that snare 7 provides "compressive hair capture means" (as defined supra). Structurally, compressive hair capture means comprises:

(a) mounting members 18A and 18B being both (i) flexibly compressive within a guide chamber having walls 22A/22B and (ii) springably self-opening and self-closing when exiting or entering, respectively, through orifices 5S and 5B;

(b) hair snare fibers 19 being flexible and of a length and curvature to allow compressibility of snare 7 within the guide chamber formed by walls 22A/22B;

(c) guide chamber walls 22A/22B being of such a diameter and shape as to allow slideable exiting and entry of snare 7;

(d) the size and shape of orifices 5A and 5B being effective as to allow entry of hair entrapped within snare 7 according to the process disclosed (supra); and, (e) cutting surfaces 13A/B/C/D in orifice 5A lying at substantially an angle and having substantially a shape suitable for exit of, and compressible entry of, snare 7, as well as, snare 7 carrying entrapped hairs 25.

In alternative embodiments, in regard to the instant loop capture snare 7 of FIGS. 4A and 4B, hair entrapment is achieved when an operator inserts the proximal ends of a test subjects hair into snare loop 7. With this device hair capture is achieved by pushing barrel 1 toward the scalp of a test subject while at the same time pulling in a proximal direction on handle cap 3, i.e., referred to herein as an alternative "push-pull device". The net result of the latter two actions being to move the barrel toward the scalp while guiding the hair sample through orifices 5A and 5B, into the storage/extraction vessel 9 lumen 11. In certain alternative embodiments (as presently envisaged), the instant loop snare 7 (FIG. 4B) comprises a flexible slip-knot loop, wherein a hair test sample is first entrapped, i.e., within the loop, and then compressibly captured as the volume of the loop is progressively decreased as the pulling pressure is applied by the operator, i.e., similar to a cattleman's lariat.

The alternative hair snare 7 embodiments schematically depicted in FIGS. 4C, 4D, 4E and 4F may be used interchangeably in the device of FIG. 1A or the "push-pull" device of FIG. 4A (supra).

In other embodiments, the invention provides sub-components for a hair collection device according to FIG. 1A. The subject sub-components provide advantages of being relatively easy to assemble. The sub-component parts are as follows: namely, (i) an integral hair snare shaft 4/snare 7 sub-component part (i.e., FIG. 1B minus cap 3); (ii) a hair snare handle/cap 3 sub-component part (i.e., only the cap 3 of FIG. 1B/2A); (iii) a storage/extraction vessel 9 sub-component part (FIG. 1D); and, (iv) a barrel 1 sub-component part (FIG. 1C).

In other embodiments, the invention provides a process for assembling the instant hair collection device of FIG. 1A according to the following steps: namely, (i) Assembly is initiated by inserting the distal 12 end of storage/extraction vessel 9 (FIG. 1D) into barrel 1 lumen 8 (FIG. 1C) and slideably engaging the vessel 9 until boss 10 (FIG. 1D) is engaged upon the proximal boundary of barrel 1 (FIG. 1C);

(ii) Storage/extraction vessel 9 is rotated within the barrel 1 lumen 8 until orifices 5A and 5B are aligned to form a entry opening into the storage lumen 11 of extraction vessel 9 (FIG. 1E/1F).

(iii) The proximal end of shaft 4 of the hair snare shaft 4/snare 7 sub-component part is next introduced through the entry opening formed by orifices 5A/5B, into guide chamber 22A/22B (FIG. 2D), then through the passage in guide chamber top 23 (FIG. 2D) into the storage/extraction vessel 9 lumen 11 (FIG. 1C), then slideably up through storage lumen 11 into sleeve 2 (FIG. 1D), then to finally extend beyond the proximal margin of sleeve 2 (FIG. 1A);

(iv) handle/cap 3 is next aligned onto the extending proximal end of shaft 4/snare 7 such that snap clips 16A/16B in recess 15 (FIG. 2B) are positioned to accept shaft 4 prongs 17A/17B (FIG. 2B); and, (v) pressure is applied to the handle/cap 3 (FIG. 1B/2A) and the snare 7 (FIG. 1B/2A) sufficient to engage snap clips 16A/16B and prongs 17A/17B (FIG. 2B), thereby securing handle/cap 3, i.e., both on the hair snare shaft 4 (FIG. 1B) and within storage/extraction vessel 9 lumen 11 (FIG. 1A).

Skilled artisans will of course recognize a variety of sizes, shapes and conformations that are effective to achieve the instant "entrapment means" and "compressible hair capture means". Dimensions are thus provided, by way of illustration, not by way of limitation. The diameter of the instant hair collection device barrel 1 may be adjusted to accommodate different volumes of hair sample, e.g., from about 5 mm to about 20 mm, preferably about 5 mm to about 15 mm, most preferably, about 4 mm to about 7 mm. Likewise, the size and shape of orifices 5A/5B (FIG. 1F) may be adjusted, in different embodiments, to receive different volumes of a hair sample, e.g., from a circular or elliptical diameter of about 3 mm to about 5 mm, to a circular or elliptical diameter of about 8 mm to about 12 mm.

Figure 4H:
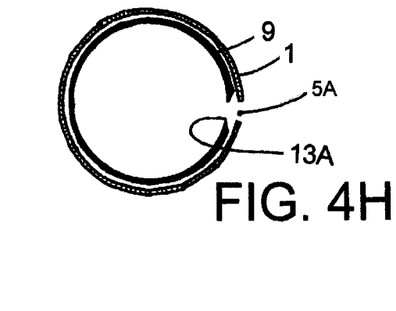
FIG. 4H depicts schematically an alternative embodiment with hair cutting surfaces located at the margins of the inner extraction vessel portion, rather than within the outer barrel portion (FIG. 1E), as disclosed further below.

Materials suitable for use in constructing the instant device include a variety of hydrocarbon plastic polymers and co-polymers and metallic alloys. The barrel 1, storage/extraction vessel 9, and handle/cap 3 sub-components preferably comprise a rigid material, e.g., a metal, a polyester, a polyamide, a polystyrene, a polycarbonate, a polyethylene, a polypropylene, a polybutylene, a polyvinyl, a vinyl chloride or a vinyl fluoride, an acrylate, a methacrylate and a plastic co-polymer thereof. Hair snare device shaft 4 and sub-component parts, i.e., including shaft 4, mounting members 18A/18B and the plurality of snare fibers 19, are preferably formed of a rigid but flexible material; e.g., a nylon, a flexible butadiene-styrene copolymer, a semi-rigid silastic rubber and the like. In one presently preferred embodiment, fibers 19 comprise Velcro™. Barrel base 6 preferably comprises a pliable, soft and/or flexible material which will not irritate the scalp of a test subject, e.g., a latex, a silastic rubber and the like. In alternative embodiments, storage/extraction vessel 9 may be fabricated from a metal, an alloy metal, e.g., stainless steel and the like, or from a silicon-based ceramic, e.g., a glass, a porcelain, a sintered glass and the like. Cutting surfaces 13A/B/C/D in either of orifice 5A (FIG. 1E) or orifice 5B (FIG. 4H) are preferably of a hardened sharpenable material, e.g., a metal or a hard plastic polymer. The subject cutting surfaces may be serrated or curved, and integral with, or attached with a fastener or an adhesive to, barrel 1 (FIG. 1E) or to extraction vessel 2 (FIG. 4H).

Manufacture of the sub-component parts may accomplished by a variety of methods known to those of skill in plastics, e.g. by blow or form molding, hot pressing, vacuum pressing, molding, machining and the like.

While the preferred embodiment of the invention has been illustrated and described, it will be appreciated that various changes can be made therein without departing from the spirit and scope of the invention.

We claim:

1. A hair collection device comprising:
    an outer barrel having a barrel lumen with a first hair collection oriface;
    an inner hair storage container insertable in a distal direction within and removable in a proximal direction from the barrel lumen, said inner hair storage container comprising a hair storage lumen and a second hair collection oriface; and
    a hair snare insertable in a distal direction within and removable in a proximal direction from the hair storage lumen and extendable through both of said first and second hair collection orifaces when the hair snare and the hair storage lumen are inserted into said outer barrel and the first and second orifaces are aligned relative to one another to form an entry passage into said storage lumen;
    wherein said hair snare comprises a hair snare entrapment means.

2. The hair collection device of claim 1, wherein said hair snare entrapment means comprises a loop, a slip-knot, a Venus fly trap, a brush, a coil, a spring or an adhesive pad.

3. The hair collection device of claim 1, wherein said Venus fly trap hair snare entrapment means comprises a plurality of flexible snare fibers.

4. The hair collection device of claim 1, wherein said hair snare entrapment means is capable of capturing about 5 to about 50 test subject hairs.

5. The hair collection device of claim 4, wherein said hair snare entrapment means is capable of capturing about 10 to about 50 test subject hairs.

6. The hair collection device of claim 5, wherein said hair snare entrapment means is capable of capturing about 10 to about 20 test subject hairs.

7. The hair collection device of claim 1, wherein said inner hair storage container comprises a vessel capable of retaining about 5 to about 50 test subject hairs having a hair length of about 3 cm to about 8 cm.

8. The hair collection device of claim 1, wherein one or both of said first and second hair collection orifaces comprise a cutting surface.

9. The hair collection device of claim 8, wherein said cutting surface is capable of cutting a hair test sample when said hair test sample extends through both of said first and second hair collection orifaces and when said hair storage container is either rotated relative to said outer barrel or is moved in a proximal direction relative to said outer barrel.

10. The hair collection device of claim 1, further comprising a compressive hair capture means.

11. The hair collection device of claim 10, wherein said compressive hair capture means comprises a flexibly self-opening and self-closing hair snare fiber mounting member and a guide chamber in said inner hair storage container, wherein said guide chamber comprises wall members capable of retaining and compressing said flexible mounting member when said snare is resident within said guide chamber and said flexible mounting member.

12. The hair collection device of claim 1, wherein said inner hair storage container further comprises a vessel suitable for extracting a hazardous material from a hair test sample.

13. The hair collection device of claim 12, wherein said inner hair storage container comprises a material that is chemically inert in an organic solvent, an acid, a base or a supercritical fluid.

14. The hair collection device of claim 13, wherein said material comprises a metal, a ceramic, a glass or a plastic polymer or co-polymer.

15. The hair collection device of claim 1, wherein said outer barrel and said inner hair storage container are each substantially cylindrical, eliptical, square or rectangular.

16. The hair collection device of claim 15, comprising a device having an overall cylindrical or eliptical diameter of about 5 mm to about 20 mm and a length of about 9 cm to about 15 cm.

17. The hair collection device of claim 16, wherein said device comprises a diameter of about 8 mm to about 12 mm and a length of about 10 cm to about 14 cm.

18. A process for collecting a hair test sample from a hair surface of a test subject, wherein said hair test sample comprises a plurality of hair strands and said process comprises the steps of:
    engaging a hair collection device with the hair surface of the test subject, wherein said hair collection device comprises a hair collection orifice having as edges thereto one or more cutting surfaces;
    introducing a hair entrapment means through said hair collection orifice;
    engaging said hair entrapment means with one or more of said plurality of hair strands;
    removing said hair entrapment means from said hair collection orifice thereby effectively bringing said entrapped hair strands through said hair collection orifice;
    bringing said cutting surfaces into apposition with said hair strands in a manner effective to cut said hair strands and effect said collection of said test sample.

19. A process for assembling a hair collection device from manufactured sub-component parts, wherein said parts comprise:
    an outer barrel having a barrel lumen;
    an inner hair storage container insertable within and removable from the barrel lumen, said inner hair storage containing comprising a storage lumen; and
    a hair snare insertable within and removable from the storage lumen and further comprising both a handle portion and a hair entrapment means; and,
    and wherein said process comprises the steps of:
        inserting the inner hair storage container into the barrel lumen; and,
        inserting the hair snare into the storage lumen thereby effecting assembly of the hair collection device from its manufactured component parts.

* * * * *